US009182658B2

(12) United States Patent
Kristoffersen et al.

(10) Patent No.: US 9,182,658 B2
(45) Date of Patent: Nov. 10, 2015

(54) TRANSMIT BEAMFORMING IN 3-DIMENSIONAL ULTRASOUND

(75) Inventors: Kjell Kristoffersen, Oslo (NO); Bruno Hans Haider, Ballston Lake, NY (US); Thomas Halvorsroed, Tolvsroed (NO); Steinar Bjaerum, Horten (NO)

(73) Assignee: General Electric Company, Schenectady, NY (US)

( * ) Notice: Subject to any disclaimer, the term of this patent is extended or adjusted under 35 U.S.C. 154(b) by 592 days.

(21) Appl. No.: 13/332,253

(22) Filed: Dec. 20, 2011

(65) Prior Publication Data

US 2012/0095344 A1    Apr. 19, 2012

Related U.S. Application Data

(63) Continuation of application No. 11/770,126, filed on Jun. 28, 2007, now Pat. No. 8,096,951.

(51) Int. Cl.

| *A61B 8/14* | (2006.01) |
|---|---|
| *G03B 42/06* | (2006.01) |
| *G01S 15/89* | (2006.01) |
| *H04B 1/02* | (2006.01) |

(Continued)

(52) U.S. Cl.
CPC .............. *G03B 42/06* (2013.01); *A61B 8/4461* (2013.01); *A61B 8/4483* (2013.01); *G01S 15/8925* (2013.01); *G01S 15/8927* (2013.01); *A61B 8/4488* (2013.01); *A61B 8/4494* (2013.01); *A61B 8/483* (2013.01); *B06B 2201/76* (2013.01)

(58) Field of Classification Search
CPC .. A61B 8/4461; A61B 8/4483; A61B 8/4488; A61B 8/4494; A61B 8/483; G03B 42/06; G01S 15/8925; G01S 15/8927; B06B 2201/76
USPC ........................................... 600/459; 367/138
See application file for complete search history.

(56) References Cited

U.S. PATENT DOCUMENTS

| 4,045,800 A | * | 8/1977 | Tang et al. ..................... 342/372 |
|---|---|---|---|
| 5,375,470 A | * | 12/1994 | Matsushima et al. ........... 73/626 |

(Continued)

FOREIGN PATENT DOCUMENTS

| JP | 2000-325344 A | 11/2000 |
|---|---|---|
| JP | 2005-342194 A | 12/2005 |

OTHER PUBLICATIONS

English translation of Foreign Official Action from Japan, Application No. 2008-159813, Drafting Date: Jul. 10, 2013, (3) pgs.

*Primary Examiner* — Long V Le
*Assistant Examiner* — Angela M Hoffa
(74) *Attorney, Agent, or Firm* — Dean D. Small; The Small Patent Law Group, LLC

(57) ABSTRACT

An ultrasound system comprises a probe including a two-dimensional (2D) array of transducer elements that form an aperture having a plurality of receive elements that are configured to receive ultrasound signals. The transducer elements form at least one transmit sub-aperture that is configured to be interconnected with a fixed group of the transducer elements within the aperture. Transmitters generate electrical transmit signals, and at least one transmit sub-aperture processor (tx SAP) maps the transducer elements within the fixed group of the transducer elements to the transmitters in a transmit configuration based on a beam steering direction.

18 Claims, 15 Drawing Sheets

(51) Int. Cl.
  *A61B 8/00* (2006.01)
  *A61B 8/08* (2006.01)

(56) References Cited

U.S. PATENT DOCUMENTS

| | | | | |
|---|---|---|---|---|
| 5,573,001 A * | 11/1996 | Petrofsky et al. | | 600/447 |
| 5,832,923 A * | 11/1998 | Engeler et al. | | 600/459 |
| 6,013,032 A * | 1/2000 | Savord | | 600/443 |
| 6,126,602 A * | 10/2000 | Savord et al. | | 600/447 |
| 7,090,642 B2 * | 8/2006 | Satoh | | 600/447 |
| 7,217,243 B2 * | 5/2007 | Takeuchi | | 600/447 |
| 7,322,936 B2 * | 1/2008 | Takeuchi | | 600/447 |
| 7,527,592 B2 * | 5/2009 | Haugen et al. | | 600/447 |
| 7,775,982 B2 * | 8/2010 | Hazard et al. | | 600/462 |
| 7,798,967 B2 * | 9/2010 | Takeuchi | | 600/447 |
| 8,096,951 B2 * | 1/2012 | Kristoffersen et al. | | 600/447 |
| 2004/0122321 A1 * | 6/2004 | Alexandru | | 600/459 |
| 2005/0113694 A1 * | 5/2005 | Haugen et al. | | 600/443 |
| 2005/0113698 A1 * | 5/2005 | Kristoffersen et al. | | 600/459 |
| 2005/0113699 A1 * | 5/2005 | Haugen et al. | | 600/459 |
| 2005/0228279 A1 * | 10/2005 | Ustuner et al. | | 600/443 |
| 2006/0058670 A1 * | 3/2006 | Lin et al. | | 600/447 |
| 2007/0208254 A1 * | 9/2007 | Johnson et al. | | 600/459 |
| 2008/0027323 A1 * | 1/2008 | Freiburger | | 600/453 |
| 2008/0262351 A1 * | 10/2008 | Scampini | | 600/443 |

* cited by examiner

# TRANSMIT BEAMFORMING IN 3-DIMENSIONAL ULTRASOUND

CROSS REFERENCE TO RELATED APPLICATIONS

This application is a continuation of and claims priority and the benefit of the filing date of U.S. application Ser. No. 11/770,126, filed Jun. 28, 2007 and entitled "TRANSMIT BEAMFORMING IN 3-DIMENSIONAL ULTRASOUND", the subject matter of which is hereby incorporated by reference in its entirety.

BACKGROUND OF THE INVENTION

This invention relates generally to ultrasound medical imaging systems, and more specifically, to partitioning multiple transducer elements of an ultrasonic probe into non-overlapping sub-apertures for the transmission of an ultrasound signal.

Two key components of an ultrasound system are the ultrasound probe and the beamformer. The beamformer focuses and steers ultrasound energy transmitted by and received by the probe to acquire image data, and as one step in generating images of anatomic content on a display. Three-dimensional (3D) ultrasound imaging may be accomplished using a probe that has a two-dimensional (2D) matrix array of transducer elements. In many systems, the elements are used for both transmit and receive operations. Current systems achieve this dual operation of the transducer elements by multiplexing between the transmit and receive circuitry in the system. Each channel in the probe may be connected with one cable to the system and be used both for transmit and receive operations.

The transducer elements are typically arranged in a 2D array that may be divided into a plurality of sub-apertures (or subarrays) for both transmit and receive operations by grouping subsets of the transducer elements together. For example, each aperture may include at least one acoustic transducer element. The sub-aperture grouping may be different on transmit and receive. The layout and implementation of the sub-apertures for transmit and receive affects image quality. Some probes use transmitters located within the probe although this configuration can generate significant heat. It is therefore desirable to provide a transmit solution for a 2D array probe where a relatively small number of system channels (such as approximately 170 system channels) can drive an array with a large number of elements (such as approximately 2600 elements).

Therefore, a need exists for improved transmit beamforming of a 2D array for 3D ultrasound imaging that improves the aperture sub-grouping without the limitations discussed above.

BRIEF DESCRIPTION OF THE INVENTION

In one embodiment, an ultrasound system comprises a probe including a two-dimensional (2D) array of transducer elements that form an aperture having a plurality of receive elements that are configured to receive ultrasound signals. The transducer elements form at least one transmit sub-aperture that is configured to be interconnected with a fixed group of the transducer elements within the aperture. Transmitters generate electrical transmit signals, and at least one transmit sub-aperture processor (tx SAP) maps the transducer elements within the fixed group of the transducer elements to the transmitters in a transmit configuration based on a beam steering direction.

In another embodiment, a method for transmitting ultrasound signals using a 2D array of transducer elements comprises forming at least one transmit sub-aperture comprising a fixed group of transducer elements for transmitting ultrasonic transmit signals and at least two receive sub-apertures for receiving ultrasonic receive signals. The at least one transmit sub-aperture and the at least two receive sub-apertures are associated with a predetermined group of system channels. A delay is calculated for each of the transducer elements within the fixed group of transducer elements wherein the delay is based at least on a steering angle associated with the transducer element and a transmit operation. At least a portion of the transducer elements within the fixed group of transducer elements are connected to the predetermined group of system channels based at least on the delays associated with the transducer elements.

In yet another embodiment, an ultrasound system comprises a probe including a 2D array of transducer elements that form an aperture having a plurality of receive elements that are configured to receive ultrasound signals. At least one configurable cross-point switch has first and second sides and is interconnected on the first side with a fixed group of the transducer elements that forms a transmit sub-aperture configured to transmit ultrasound signals. System channels are configured to convey at least the transmit signals and interconnect with the at least one configurable cross-point switch on the second side. The at least one configurable cross-point switch further comprises at least one switch associated with each of the transducer elements within the fixed group of transducer elements, and the at least one configurable cross-point switch connects at least one of the transducer elements with one of the system channels. A sub-aperture processor (SAP) controller is configured to control the at least one configurable cross-point switch to map each of the transducer elements within the fixed group of transducer element to the system channels in a transmit configuration based on delays associated with the transmit signals.

DETAILED DESCRIPTION OF THE INVENTION

Figure 1:
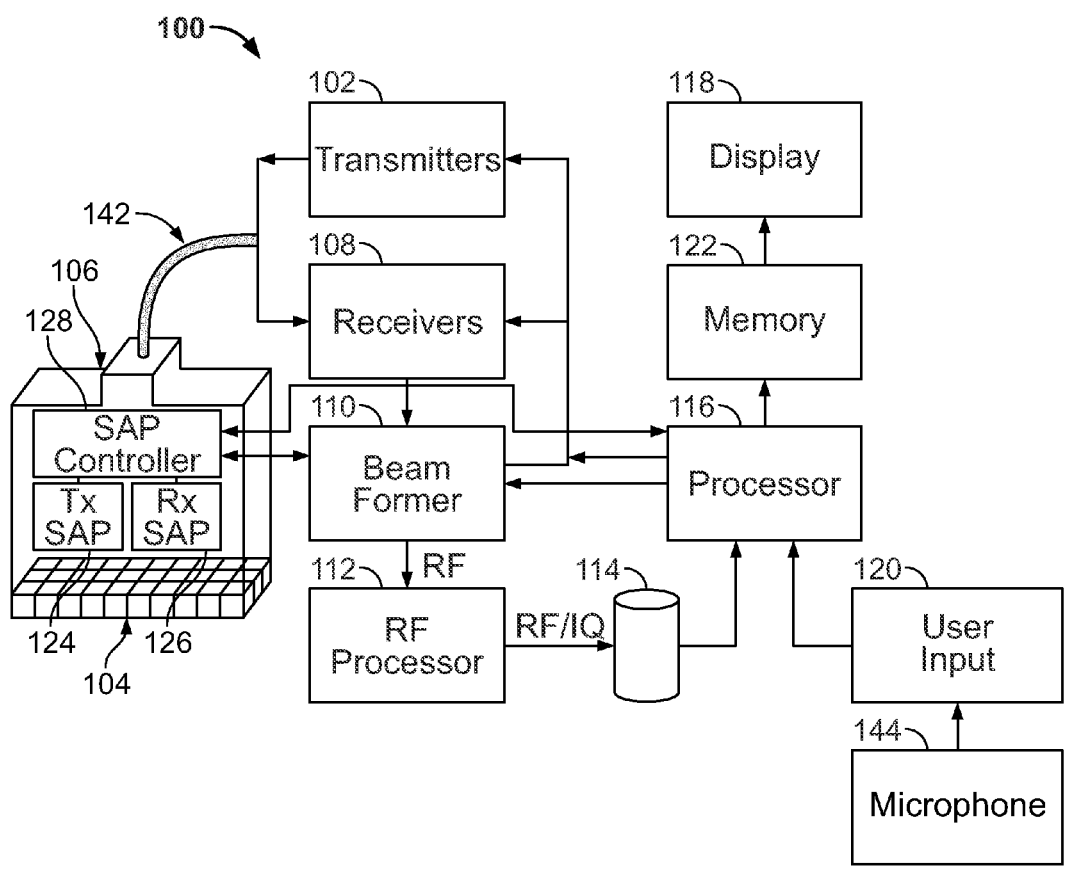
FIG. 1 is a block diagram of an ultrasound system formed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

FIG. 1 illustrates a block diagram of an ultrasound system 100. A probe 106 is connected to the system 100 via cable 142. The probe 106 has a two-dimensional (2D) matrix array of transducer elements 104 and is capable of three-dimensional (3D) scanning. System channels (not shown) may be within the cable 142 and may convey transmit and receive signals to and from the probe 106. Alternatively, separate transmit channels and receive channels may be used. At least one transmit (tx) sub-aperture processor (SAP) 124 and one receive (rx) SAP 126 is within the probe 106 for transmit and/or receive operations. In another embodiment, one tx/rx SAP may facilitate both of the receive and transmit functions. A SAP controller 128 communicates with system processor 116 and/or beamformer 110. The SAP controller 128 also communicates with the SAP(s) 124 to configure transmit and receive sub-apertures by connecting particular transducer elements 104 with system channels (or transmit and receive channels) that are used to convey the ultrasonic signals to and from the probe 106. The SAP controller 128 may be implemented in hardware or software, or a combination thereof, and may alternatively be located within the system 100, such as within the processor 116.

The ultrasound system 100 includes transmitters 102 that drive the transducer elements 104 within the probe 106 to emit pulsed ultrasonic signals into a body. The transmitters 102 are located outside of the probe 106, such as within a housing (not shown) that encloses the internal components of the system 100. Beamformer 110 supplies information to the transmitters 102 such as steering information, for example, provided as steering signals. The steering information may be different across the array of transducer elements 104. The SAP controller 128 further communicates with the tx SAPs 124 and rx SAPs 126 to control the local steering direction of the individual sub-apertures (based upon the steering/focusing of the transmit and receive beams respectively).

The transmitted ultrasonic signals are back-scattered from structures in the body, like blood cells or muscular tissue, to produce echoes that return to the transducer elements 104. The returning echoes are converted by the transducer elements 104 back to electrical energy that is received by a plurality of receivers 108. The received signals are passed through the beamformer 110 that performs receive beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to an RF/IQ buffer 114 for temporary storage.

A user input 120, which may be configured as a user interface having a keyboard, mouse, trackball, control buttons, etc., may be used to control operation of the ultrasound system 100, including, to control the input of patient data, scan parameters, to select or identify a focal point or region of interest, and the like, and may also include using voice commands provided via a microphone 144. Other various embodiments may include a set of user controls that may be configured for controlling the ultrasound system 100 and may be provided, for example, as part of a touch screen or panel, and/or as manual inputs, such as user operable switches, buttons, and the like. The set of user controls may be manually operable or voice operated.

The ultrasound system 100 also includes the processor 116 (e.g., a processor module) to process the acquired ultrasound information (i.e., RF signal data or IQ data pairs) and prepare frames or volumes of ultrasound information for display on display 118. The display 118 has a known resolution that may be defined in terms of pixels or other known parameter. The processor 116 is adapted to perform one or more processing operations according to a plurality of selectable ultrasound modalities on the acquired ultrasound information. Acquired ultrasound information may be processed in real-time during a scanning session as the echo signals are received.

It should be understood that the functionality discussed with respect to the system 100 is not limited to any ultrasound system type. For example, the system 100 may be housed within a cart-based system or may be implemented in a smaller, portable system as discussed in FIG. 2.

Figure 2:
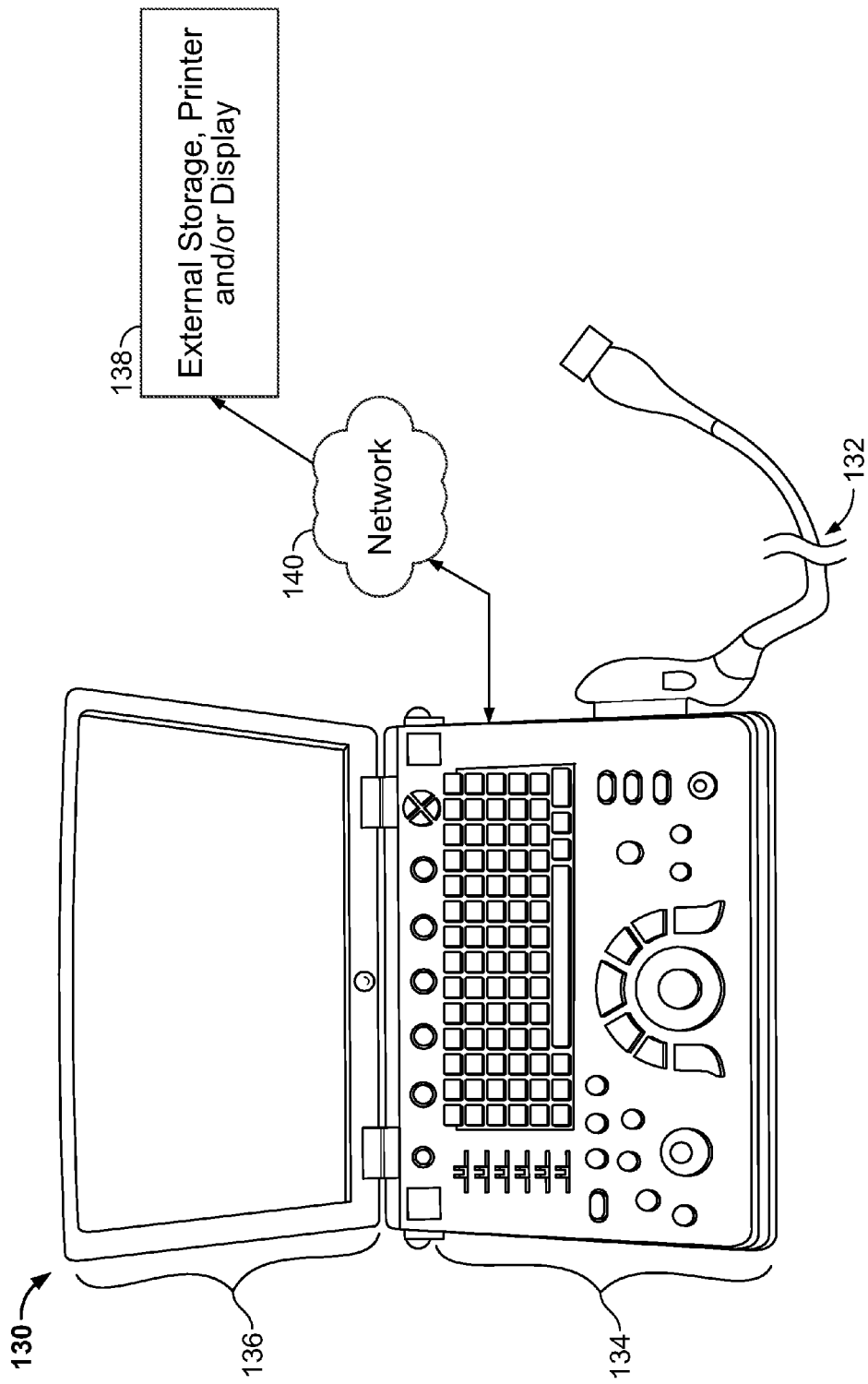
FIG. 2 illustrates a miniaturized ultrasound system formed in accordance with an embodiment of the present invention and having a probe configured to acquire ultrasonic data.

FIG. 2 illustrates a 3D-capable miniaturized ultrasound system 130 having a probe 132 configured to acquire 3D ultrasonic data. Although not shown, the probe 132 has a 2D array of transducer elements 104 as well as the tx SAPs 124 and rx SAPs 126 as discussed previously with respect to the probe 106 of FIG. 1. A user interface 134 (that may also include an integrated display 136) is provided to receive commands from an operator. As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer, for instance, having dimensions of approximately 2.5 inches in depth, approximately 14 inches in width, and approximately 12 inches in height. The ultrasound system 130 may weigh about ten pounds, and thus is easily portable by the operator. The integrated display 136 (e.g., an internal display) is also provided and is configured to display a medical image.

The ultrasonic data may be sent to an external device 138 via a wired or wireless network 140 (or direct connection, for example, via a serial or parallel cable or USB port). In some embodiments, external device 138 may be a computer or a workstation having a display. Alternatively, external device 138 may be a separate external display or a printer capable of receiving image data from the hand carried ultrasound system 130 and of displaying or printing images that may have greater resolution than the integrated display 136.

As another example, the ultrasound system 130 may be a 3D capable pocket-sized ultrasound system. By way of example, the pocket-sized ultrasound system may be approximately 2 inches wide, approximately 4 inches in length, and approximately 0.5 inches in depth and weigh less than 3 ounces. The pocket-sized ultrasound system may include a display, a user interface (i.e., keyboard) and an input/output (I/O) port for connection to the probe (all not shown). It should be noted that the various embodiments may be implemented in connection with a miniaturized ultrasound system having different dimensions, weights, and power consumption.

Figure 3:
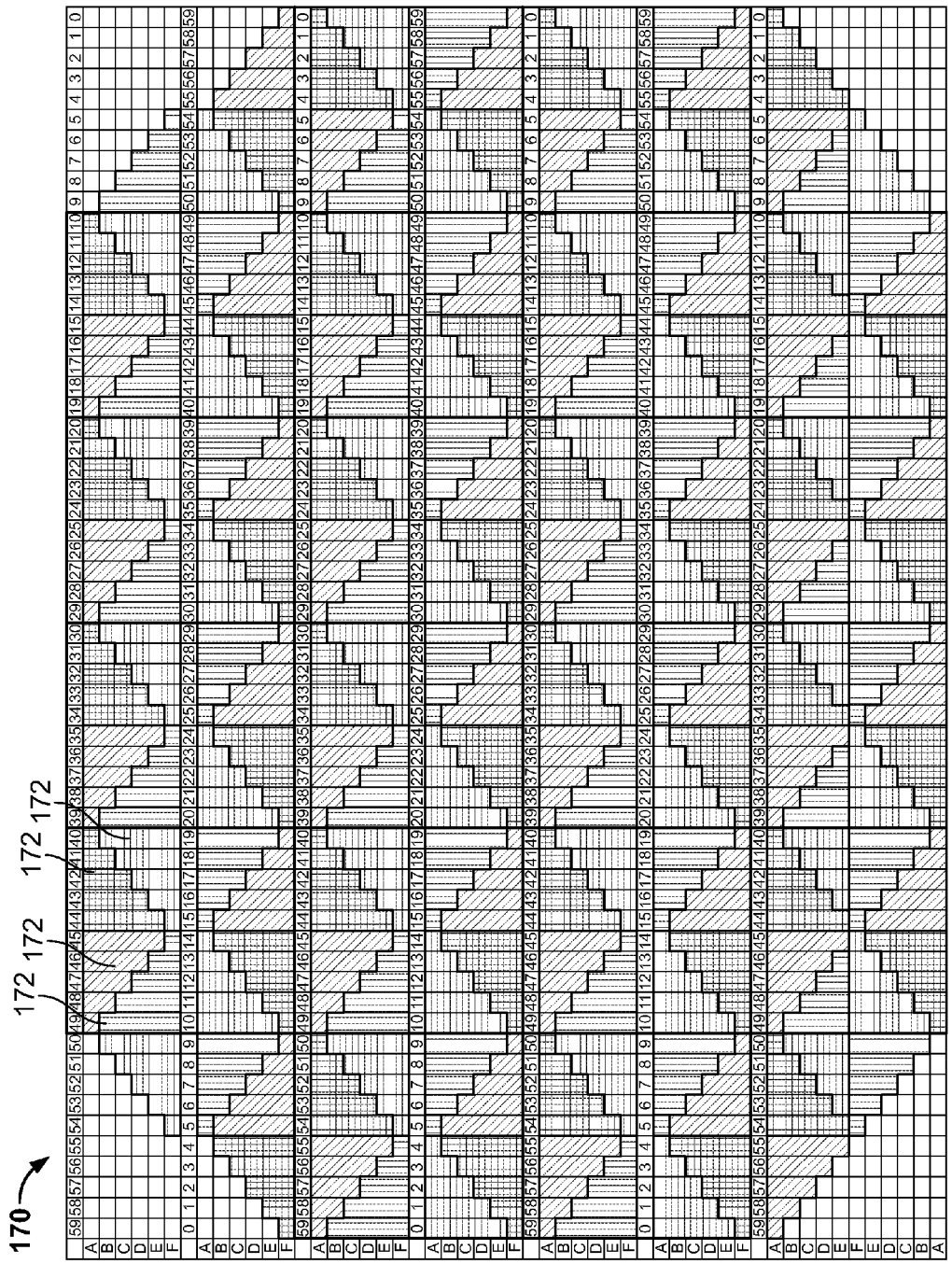
FIG. 3 is a diagram illustrating an aperture of an ultrasonic 2D array comprising transducer elements that is formed in accordance with an embodiment of the present invention.

FIG. 3 illustrates an aperture 170 extending across the face of an ultrasonic probe, such as the probe 106 of FIG. 1 that comprises a large number of transducer elements 104 arranged as a 2D array. The aperture 170 is divided into a plurality of receive sub-apertures 172 that are illustrated as triangular in this embodiment. In this example, there are 176 different receive sub-apertures 172. Each of the receive sub-apertures 172 comprise 15 transducer elements 104 (FIG. 1). Each of the receive sub-apertures 172 is connected to one channel of the beamformer 110 through a rx SAP, such as rx SAP 126. During ultrasound reception the signals received by the transducer elements 104 are passed through independent delays (or phase shifters) within the rx SAP 26 and summed together to a single output that is connected to the associated system channel.

Figure 4:
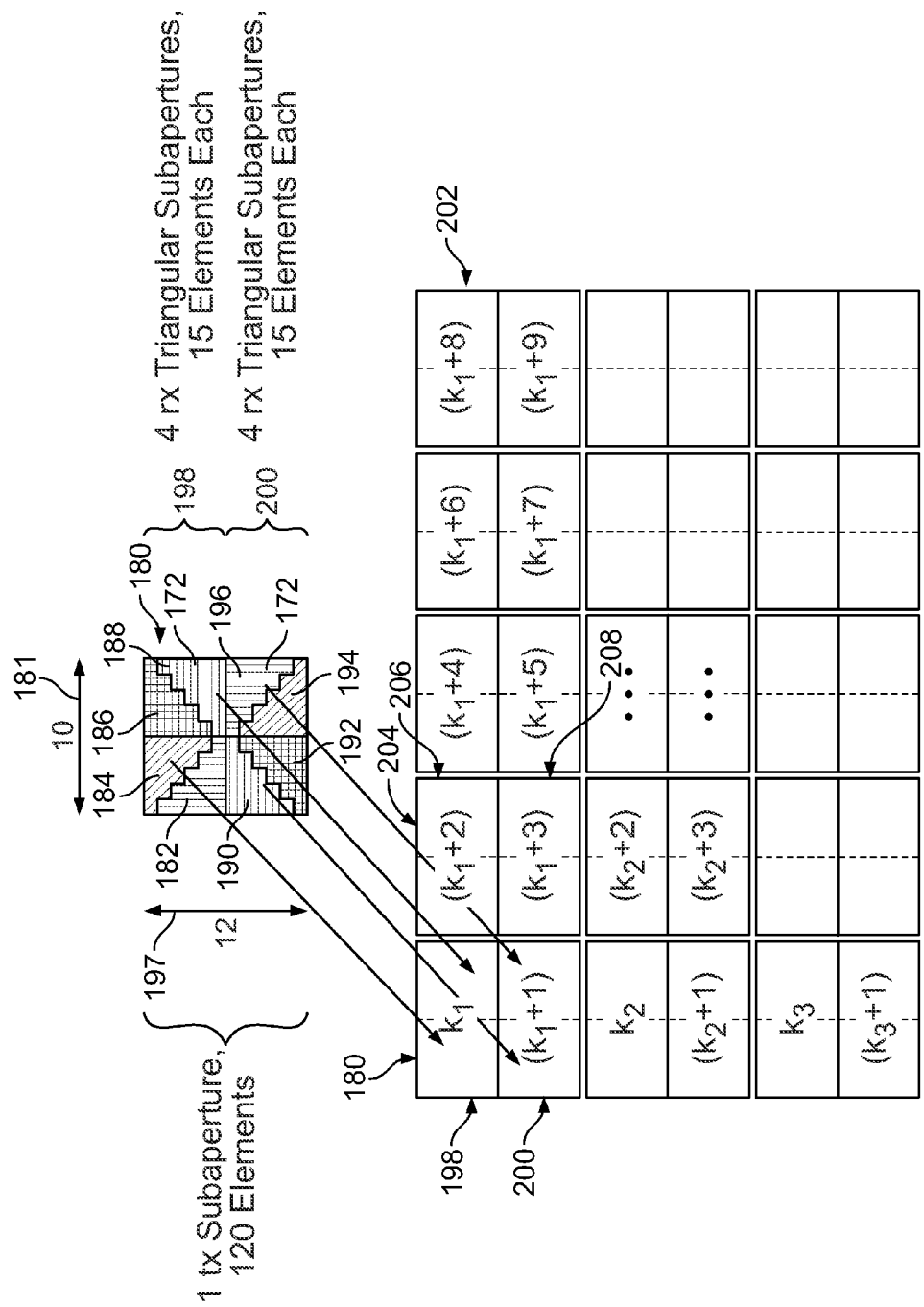
FIG. 4 is a diagram illustrating many transmit sub-apertures and a portion of the transmit sub-aperture organization formed in accordance with an embodiment of the present invention.

FIG. 4 illustrates a transmit sub-aperture 180 and a portion 202 of the transmit sub-aperture organization in a 2D array. The portion 202 illustrates a plurality of the transmit sub-apertures 180 organized in non-overlapping rectangular sub-arrays. Each transmit sub-aperture 180 comprises eight triangular receive sub-apertures 172, each of which has 15 transducer elements 104 as discussed previously. Therefore, the transmit sub-aperture 180 has a total of 120 transducer elements 104 arranged such that ten adjacent transducer elements 104 extend along a horizontal (azimuthal) axis 181 and twelve adjacent transducer elements 104 extend along a vertical (elevational) axis 197. Other configurations of the receive sub-apertures 172 may be used. The transmit sub-aperture 180 is repeated with a plurality of transmit sub-apertures throughout the portion 202. Each of the transmit sub-apertures is connected to a fixed group of the transducer elements 104, and each of the transmit sub-apertures within the portion 202 is connected to a different fixed group of transducer elements 104. For example, the transmit sub-aperture 180 is connected to the fixed group of the 120 transducer elements 104 formed by first and second element groups 198 and 200.

During transmission of an ultrasound pulse, eight channels associated with eight receive sub-apertures 182-194 drive the transducer elements 104 within the transmit sub-aperture 180. As discussed below, each of the transducer elements 104 may be connected to any of the eight channels and is not limited by the configuration of the receive sub-apertures 182-194.

In one embodiment, signals received from four adjacent receive sub-apertures 172 along the horizontal axis 181, such as first, second, third and fourth receive sub-apertures 182, 184, 186 and 188 are processed within a first integrated circuit containing four rx SAPs (not shown) and fifth, sixth, seventh, and eighth receive sub-apertures 190, 192, 194, and 196 are processed within a second integrated circuit (not shown) that may be identical to the first integrated circuit. The first through fourth receive sub-apertures 182-188 form a first element group 198 and the fifth through eighth receive sub-apertures 190-196 form a second element group 200. The first and second element groups 198 and 200 are also referred to as element groups $k_1$ and $k_1+1$, respectively, within the portion 202. A second transmit sub-aperture 204 within the portion 202 has first and second groups 206 and 208 having element groups $k_1+2$ and $k_1+3$, respectively.

Figure 5:
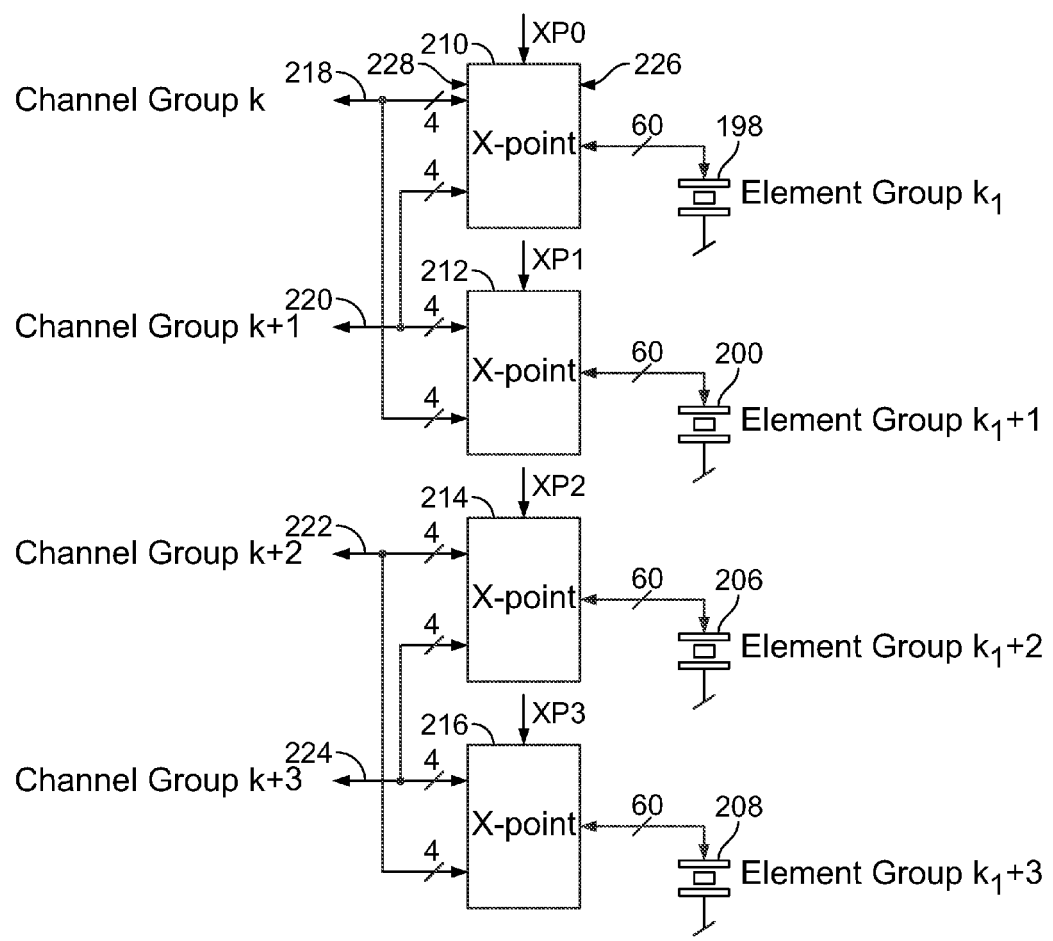
FIG. 5 is a schematic block diagram illustrating the use of a cross-point switch to connect the transducer elements to system channels that are connected to the transmitters in accordance with an embodiment of the present invention.

FIG. 5 illustrates a schematic block diagram that conceptually indicates the use of a cross-point switch to connect the transducer elements 104 to the system channels during the transmit operation. It should be understood that the receive circuitry is omitted. First, second, third and fourth cross-point switches 210, 212, 214 and 216 are illustrated and each have a plurality of switches (not shown) therein for interconnecting the transducer elements 104 and the system channels. Each of the first through fourth cross-point switches 210-216 is configuration and has a first side 226 interconnecting with the transducer elements 104 and a second side 228 interconnecting with the system channels. It should be noted that although not all of the cross-point switches are discussed, the descriptions apply to the other cross-point switches. The first cross-point switch 210 is connected to the first element group 198 (element group $k_1$) and the second cross-point switch 212 is connected to the second element group 200 (element group $k_1+1$). Eight channels are connected to each of the cross-point switches and convey signals from and to the system transmitters 102 and receivers 108, respectively, of FIG. 1. The channels are illustrated as groups of four channels wherein first and second channel groups 218 and 220 are connected to the first and second cross-point switches 210 and 212 and third and fourth channel groups 222 and 224 are connected to the third and fourth cross-point switches 214 and 216. By way of example, the combination of the first and second cross-point switches 210 and 212 may be referred to as a tx SAP 124 and the combination of the third and fourth cross-point switches 214 and 216 may be referred to as a tx SAP 124 wherein each of the tx SAPs 124 connect to eight system transmit channels to drive 120 transducer elements 104.

Each of the transducer elements 104 may be connected to one, more than one, or any of the associated channels using the cross-point switch. For a given transducer element 104 and a given transmit vector, at most one switch within the cross-point switch may be closed. In this example, there are 60 transducer elements 104 within the first element group 198 and the first and second channel groups 218 and 220 provide eight channels capable of both transmit and receive operations. Therefore, there may be up to eight switches inside the cross-point switch 210 for each of the transducer elements 104 (for a total of 480 switches) to provide the ability to connect each of the transducer elements 104 to each of the channels within the first and second channel groups 218 and 220. For a given transmit vector, the cross-point switch is programmed to select which of the 480 switches in the cross-point switch to close. The selection may be based on delays associated with the particular transducer element 104 as discussed below. At most, 60 switches (one for each transducer element 104) will be closed at a time.

Alternatively, a cross-point switch may be provided that has a lesser number of total internal switches. Therefore, one or more transducer elements 104 may be attached to one or more channels, but to less than eight channels. For example, two or four switches rather than eight switches may be available for each of the transducer elements 104 to connect to two or four channels, respectively. In another example, a subset of the transducer elements 104 may be provided with a single switch such that the transducer element 104 is always connected to the same channel when being used for transmission. In this case, other transducer elements 104 may be provided with multiple switches. Reducing the number of switches by "sparsing" the cross-point switch reduces the amount of silicon area needed to make an integrated circuit.

Figure 6:
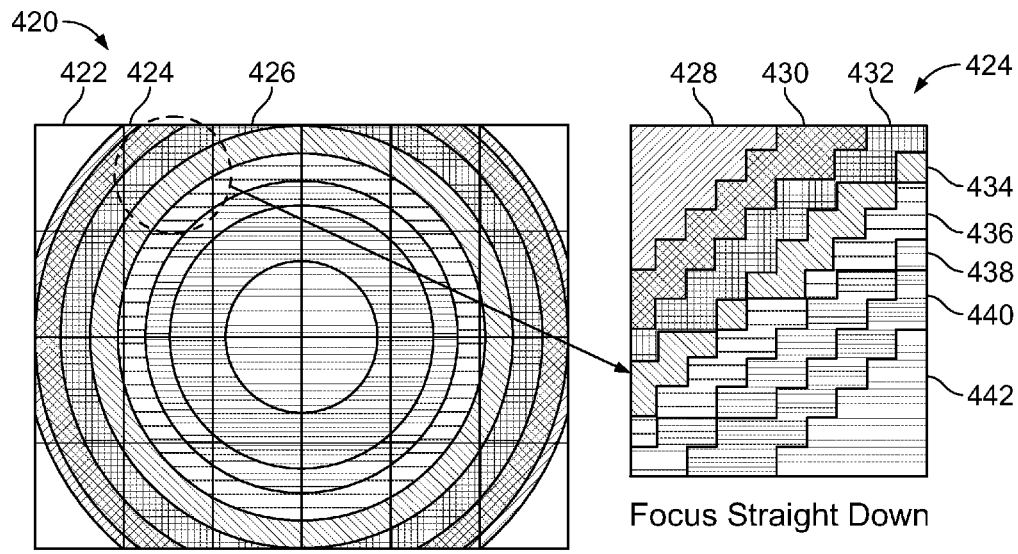
FIG. 6 illustrates an example of mapping a transmit configuration for an aperture of a probe and a transmit sub-aperture within the aperture in accordance with an embodiment of the present invention.

FIG. 6 illustrates an example of a transmit configuration. An aperture 420 is illustrated having a 2D array of transducer elements 104. In this example, the 2D array comprises 60×48 transducer elements 104. The 2D array is divided into 24 transmit sub-apertures, such as first, second and third transmit sub-apertures 422, 424 and 426, each having a 2D array of 10×12 transducer elements 104. Not all of the transmit sub-apertures are identified by item numbers.

The transducer elements 104 within each of the transmit sub-apertures are connected to a system channel to form a transmit configuration based on a beam steering direction. The beam steering direction may be based on one or more focal point, which in this example, is straight down from the probe face or straight with respect to the field of view of the probe. The transducer elements 104 of the second transmit sub-aperture 424 are illustrated in more detail. Different sets of the transducer elements 104 within the second transmit sub-aperture 424 are mapped to different channels within the eight system channels. For example, first set 428, second set 430, third set 432, fourth set 434, fifth set 436, sixth set 438, seventh set 440 and eighth set 442 of the transducer elements 104 may be mapped to the first, second, third, fourth, fifth, sixth, seventh, and eighth system channel (not shown), respectively.

Figure 7:
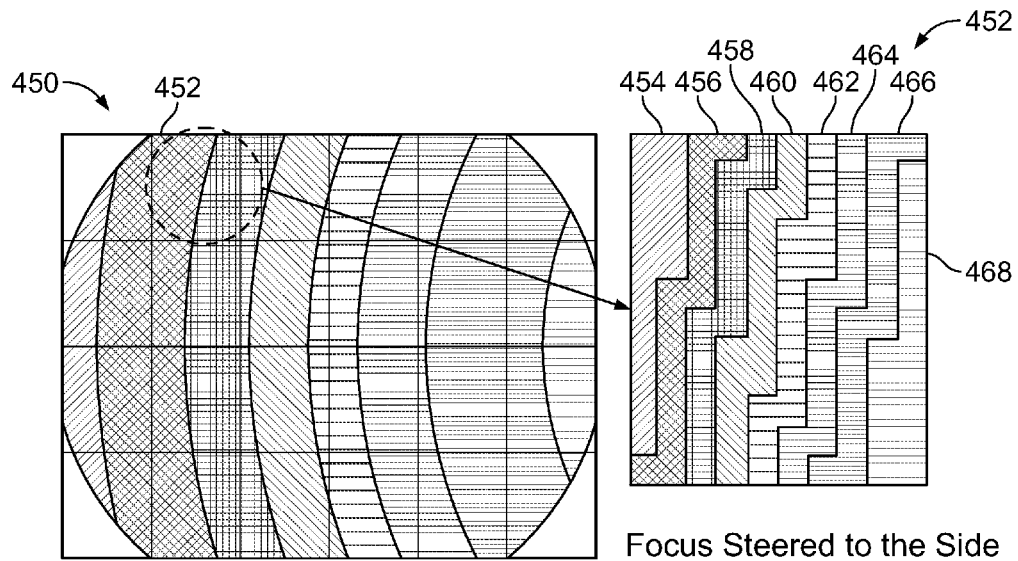
FIG. 7 illustrates another example of mapping a transmit configuration in accordance with an embodiment of the present invention.

FIG. 7 illustrates an aperture 450 that has a transmit configuration mapped to steer the focus to one side. Again, the aperture 450 is separated into 24 transmit sub-apertures and transmit sub-aperture 452 is indicated. The beam steering direction is towards one side of the field of view of the probe 106. The transducer elements 104 of the transmit sub-aperture 452 are mapped to the system channels (not shown) in the transmit configuration as shown. First set 454, second set 456, third set 458, fourth set 460, fifth set 462, sixth set 464, seventh set 466 and eighth set 468 of the transducer elements 104 may be mapped to the first, second, third, fourth, fifth, sixth, seventh and eighth system channels.

Figure 8:
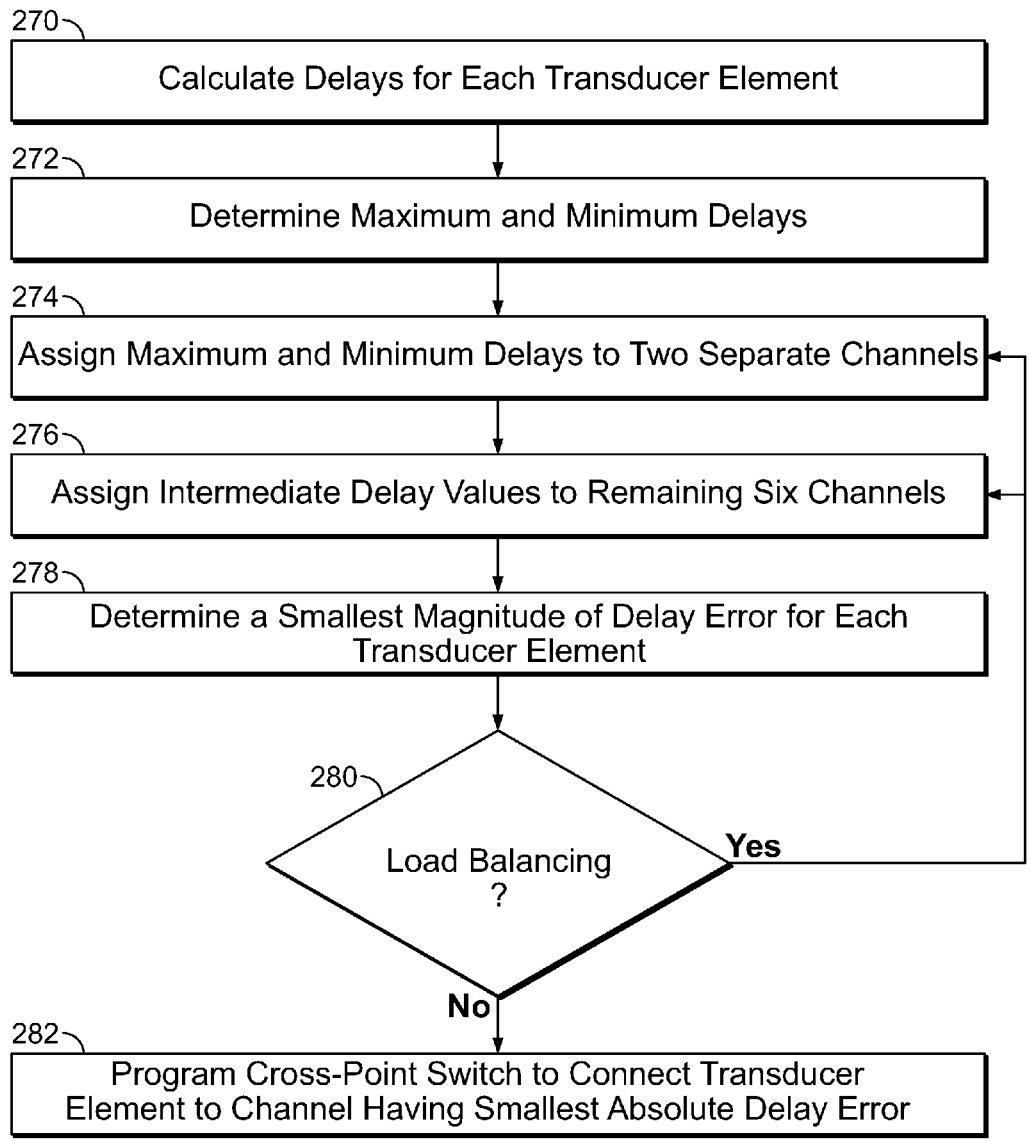
FIG. 8 is a flowchart of a method for determining a mapping of the transducer elements and channels during transmission in accordance with an embodiment of the present invention.

FIG. 8 illustrates a method for determining a mapping of the transducer elements 104 to the channels during transmission. The method may be performed for each transmit sub-aperture 180 and is performed repeatedly over the course of an ultrasonic exam to dynamically focus the ultrasound beams. At 270, the processor 116 (as shown in FIG. 1) calculates a delay for each transducer element 104. The delays may be calculated using known techniques and may be based on directional (or beam steering) set-up information specific to the transmit sub-aperture, such as based on a focal point, local steering angle or direction, and/or location within the aperture 170 (FIG. 3) of the probe 106. Alternatively, the delays may be calculated by the beamformer 110 and/or sub-aperture controller 128. At 272, the processor 116 compares the delays to determine the maximum and minimum delay. At 274, the processor 116 assigns the maximum delay and the minimum delay to two separate channels and at 276 the processor 116 assigns intermediate delay values to the remaining channels.

For example, the processor 116 may determine the delays for each of the transducer elements 104 within the first element group 198 of FIG. 5. By way of example only, the minimum delay may be zero and may be assigned to a first channel within the first channel group 218. The maximum delay may be 500 nanoseconds and may be assigned to a fourth channel within the second channel group 220. The intermediate delay values are based on the maximum and minimum delays and may be determined, for example, by using uniform quantization. The intermediate delay values are then assigned to the remaining six channels. It should be understood that any of the delays may be assigned to any channel and are not limited to the sequential example discussed herein.

In another embodiment, the transducer element 104 to channel assignment as well as the channel delay distribution (as determined at 274 and 276) may be set according to a minimized optimization criterion. Such criteria may be an average mean-square delay error or minimization of the maximum side lobe level of the transmitted beam profile.

At 278, the processor 116 compares the delay of each of the transducer elements 104 to each of the eight delays assigned to the eight channels to determine the smallest magnitude of the delay error for each transducer element 104. At 280, the processor 116 may determine whether load balancing should be accomplished to minimize variation between channels. Some of the eight channels within the first and second channel groups 218 and 220 may have many more transducer elements 104 assigned compared to other channels and thus, for a given transmit vector, the electrical load on the different transmit channels will not be the same. The system transmitters 102 have a finite output impedance and having a different load on each channel may result in some additional amplitude and/or delay variations. The series resistance of the probe cable 142 may also cause similar errors unless load balancing is done. Therefore, the method may return to 274 and/or 276 to modify the delay values assigned to one or more of the channels and determine the smallest magnitude of delay error for each transducer element 104 based on the adjusted delay values.

At 282, the sub-aperture controller 128 programs or controls the cross-point switch 210 to connect or map the transducer elements 104 to the associated channel that gives the smallest absolute delay error based on information from the processor 116. This forms a transmit configuration for the transmit sub-aperture. Each transmit sub-aperture may have a different transmit configuration, and the transmit configuration may change from beam to beam and may change over time for a transmit sub-aperture based on operator input, such as a different focal point. Continuing the example above, the cross-point switch 210 is programmed to connect each of the transducer elements 104 in the first element group 198 to one of the channels within the first and second channel groups 218 and 220 during the transmit operation. Optionally, the cross-point switch 210 may not connect all of the transducer elements 104 during each transmit operation. The transmit configuration information is communicated to the beamformer 110 and/or transmitters 102, including communicating the delays assigned to each of the system channels to the transmitters 102.

Typically, small delay errors result for transmit vectors having small steering angles. The magnitude of the delay error may increase as the amount of steering increases. To improve the beam profile for transmit beams that have larger steering angles, the maximum delay value may be constrained to, for example, two periods of the center frequency being transmitted. Transducer elements 104 that have larger delays may be "wrapped" into this domain by adding or subtracting a time corresponding to one period of the center frequency to preserve the desired phased relationship of the waveform. Alternatively, the transducer elements 104 that have delays that relatively are very large may be turned off during transmit by not assigning the transducer element 104 to any channel. This would, however, result in some degree of sparsing during transmission. Sparsing may be minimal, but may occur for some of the transmit sub-apertures 180 over the array surface or aperture 170 of the probe 106 for certain directions in space.

In addition, each switching element within the cross-point switch 210 may have a finite on-resistance. The resistance may be chosen to be significantly less than an expected electrical load (the electrical impedance of transducer elements plus interconnect capacitance). This may minimize heat generation and improve manufacturing consistency. In addition, in-probe power losses may be reduced if the transmit signal consists of a sine-line burst at the center frequency f0 with a relatively low amount of harmonics at 2*f0, 3*f0, 4*f0, and so on.

The delay errors are of concern both for the different transmit channels within one transmit vector and between different transmit vectors. For example, if the transmit vector is orthogonal to the face of the probe 106 with focus at infinite range, all of the transducer elements 104 should have the same delay, such as zero delay. In this case, it is desirable to assign a substantially identical signal to all eight transmit channels within the first and second channel groups 218 and 220 and connect fifteen transducer elements to each of the eight channels, rather then connecting 120 transducer elements 104 to one channel and leaving the remaining seven channels unused. In this example, load balancing (280 of FIG. 8) may be accomplished by redistributing the transducer elements 104 between the channels. In other embodiments, different intermediate delays may be selected to accomplish the redistribution.

The larger size of the transmit sub-aperture 180 with respect to the receive sub-apertures, such as the first through eighth receive sub-apertures 182-196 of FIG. 4, may help to reduce delay errors associated with the transducer elements 104 during transmission. Typical receive sub-aperture sizes are in the range of 15-25 transducer elements 104, while the transmit sub-aperture 180, in one embodiment, has 120 transducer elements 104. In one embodiment, the entire array may be spanned with one cross-point switch connecting all of the transducer elements 104 to all of the channels.

In some embodiments, it may be desirable to partition the transmit electronics in the same way as the receiver electronics. This is possible even if one transmit sub-aperture spans two receive ASICs. For example, returning to FIG. 4, as discussed previously the first through fourth receive sub-apertures 182-188 are processed by a first receive ASIC and the fifth through eighth receive sub-apertures 190-196 are processed by a second receive ASIC. FIG. 5 illustrates how pairs of transmit ASICs, each containing one cross-point switch of size 8×15, may be interconnected to give the topology of FIG. 4.

Figure 9:
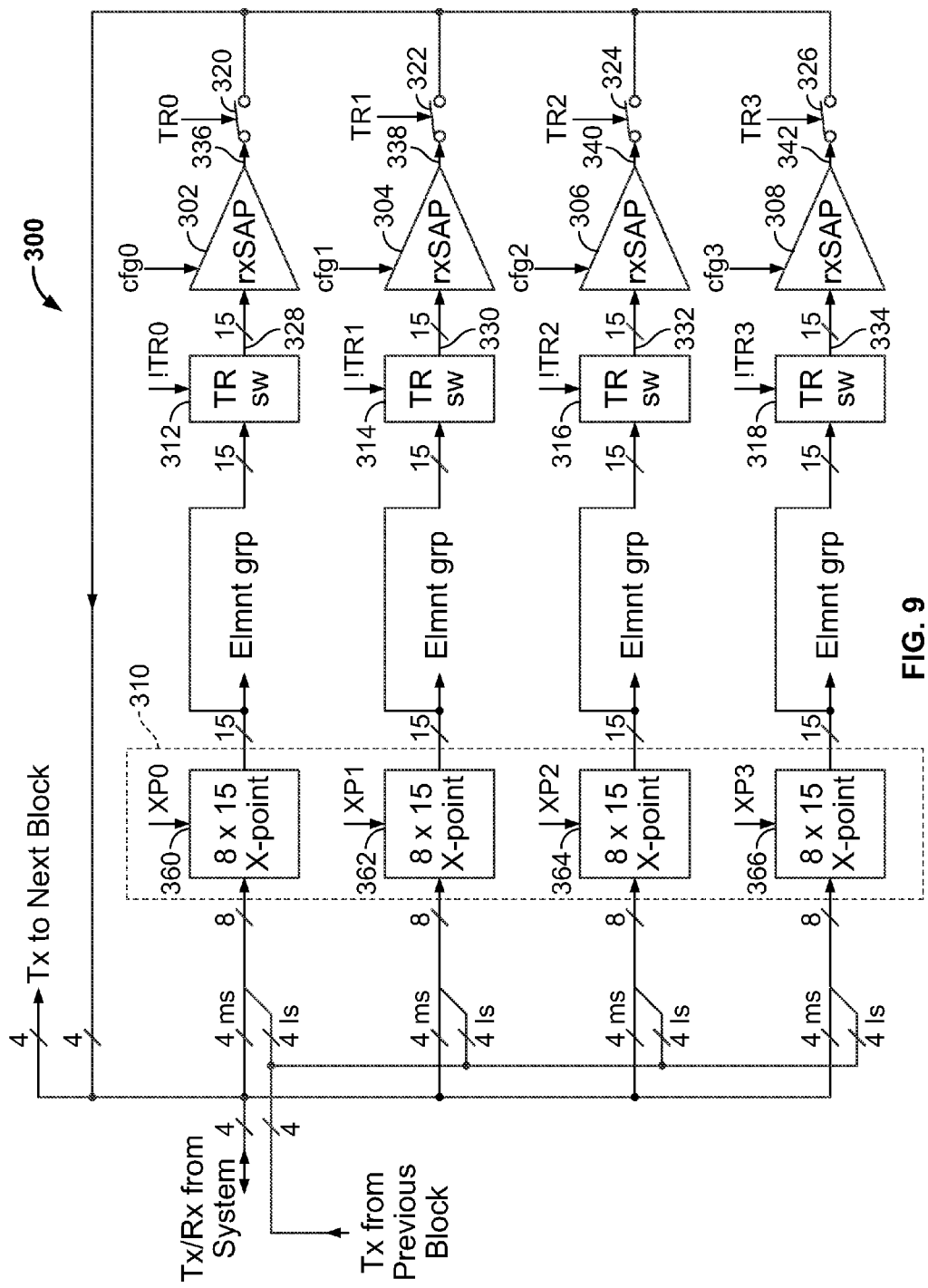
FIG. 9 is a schematic block diagram of an input/output architecture for a transmit sub-aperture processor (tx SAP) using a cross-point switch matrix that comprises switches formed in accordance with an embodiment of the present invention.

FIG. 9 illustrates a transmit/receive architecture 300 for a tx SAP using a cross-point switch matrix 310 that comprises first, second, third and fourth cross-point switches 360, 362, 364 and 366. First, second, third and fourth rx SAPs 302, 304, 306 and 308 are illustrated. The architecture 300 includes only one-half of a transmit SAP. First, second, third and fourth input transmit/receive (t/r) switches 312, 314, 316 and 318 are connected with receive input lines 328, 330, 332 and 334 to inputs of the first through fourth rx SAPs 302-308, respectively. First, second, third and fourth output t/r switches 320, 322, 324 and 326 are connected with receive output lines 336, 338, 340 and 342 to outputs of the first through fourth rx SAPs 302-308, respectively. During transmission, first, second, third and fourth input t/r switches 312-318 and the first through fourth output t/r switches 320-326 disconnect the inputs and outputs, respectively, of the first through fourth rx SAPs 302-308 to protect the first through fourth rx SAPs 302-308 from the high-voltage transmit pulses. During the reception period, the input and output t/r switches 312-326 are closed. All switches inside the cross-point switch matrix 310 are opened during reception so that the rx SAP output is not shorted.

The cross-point switches 360-366 as well as the internal beamformer settings, illustrated in FIG. 9 as the cfg0, cfg1, cfg2 and cfg3 inputs to the rx SAPs 302, 304, 306 and 308, respectively, may be controlled using, for example, a chain of shift registers, although other system architecture may be used. Each of the switches inside the cross-point switches 360-366 in one ASIC may be assigned one bit in the shift register and the value of that bit determines if the switch is open or closed.

Figure 10:
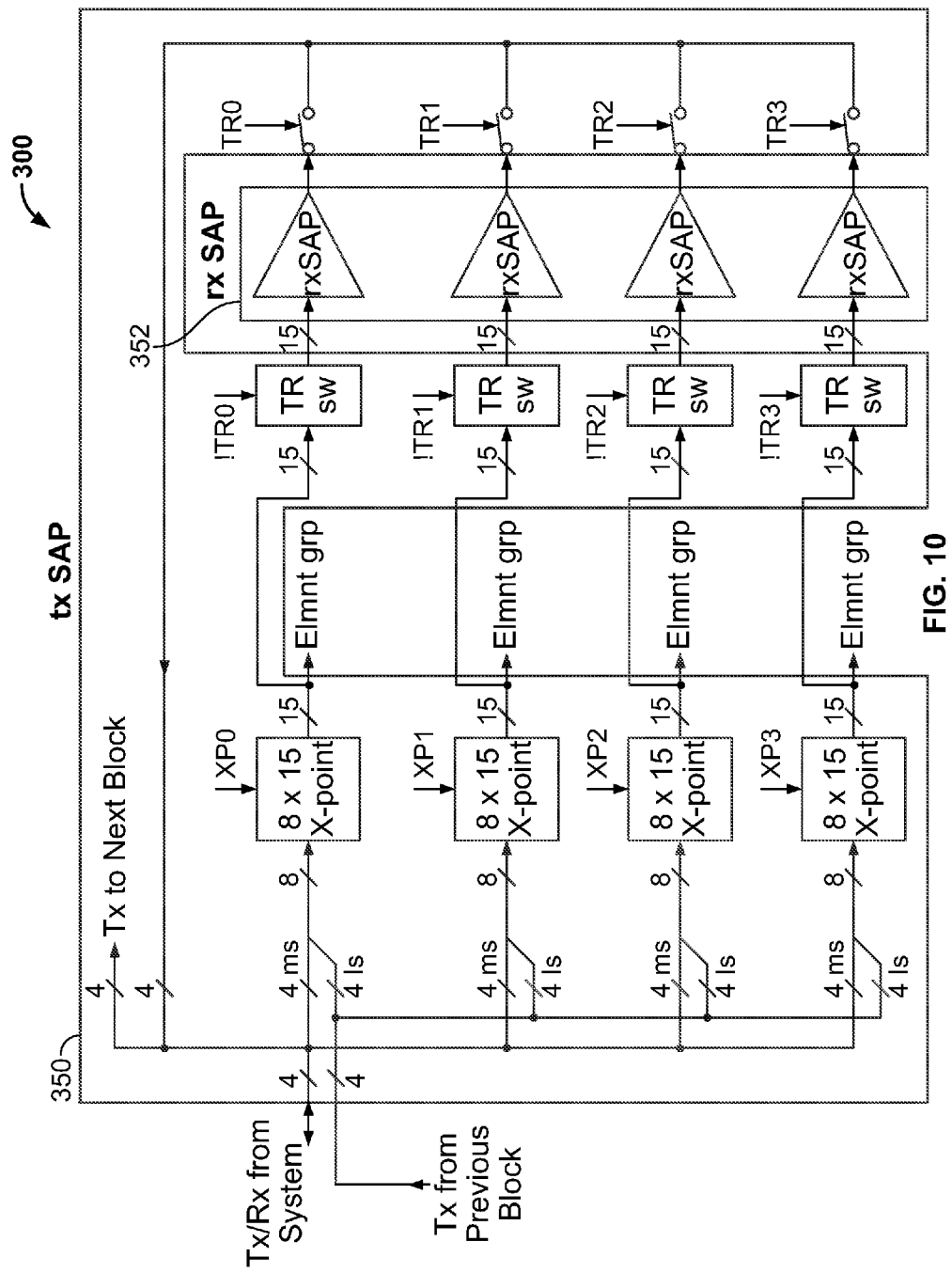
FIG. 10 is a schematic block diagram of the architecture of FIG. 9 separated into transmit and receive SAPs in accordance with an embodiment of the present invention.

FIG. 10 illustrates how the functionality of the architecture 300 of FIG. 9 may be separated into two portions, namely, a tx SAP 350 and a rx SAP 352. In one embodiment, the tx and rx SAPs 350 and 352 are formed on two separate silicon dies. The tx SAP 350 is typically formed using a silicon process with high-voltage capability, as typical transmit pulses are +/−50-100 Volts, while the rx SAP 352 may be formed in standard low-voltage silicon process. The two dies may then be stacked on top of each other. Alternatively, a single die configuration may be possible based on a silicon process that can handle high voltages and low-noise analog design, as well as digital control. Optionally, digital control electronics may be added as a third die in the stack.

Figure 11:
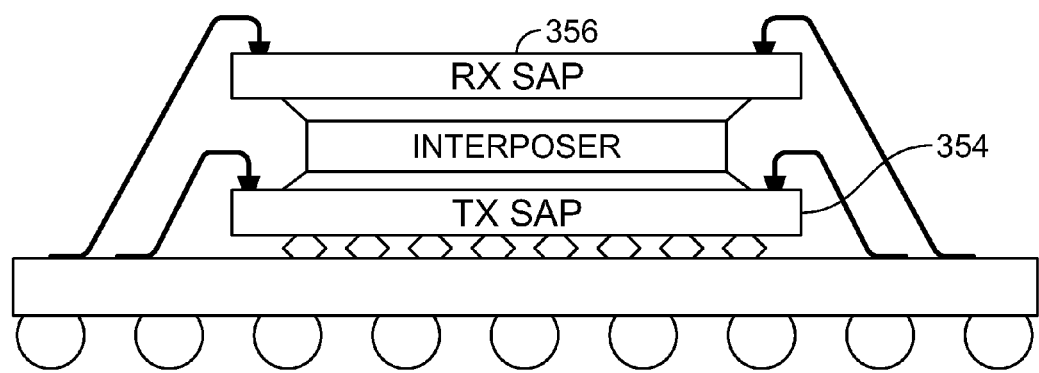
FIG. 11 is an elevation view of the stacking of transmit and receive SAPs in accordance with an embodiment of the present invention.

FIG. 11 illustrates stacking of tx and rx SAP dies 354 and 356. The stacked configuration is compact and reduces the number of off-chip connections required. For example, the fifteen receive input lines 328-334 (as shown in FIG. 9) and the receive output lines 336-342 are connected only between the tx and rx SAP dies 354 and 356 and thus an outer connection or connections to other integrated circuits (ICs) can be avoided.

Returning to FIG. 9, in one embodiment, the first through fourth input t/r switches 312-318, the first through fourth rx SAPs 302-308 and the first through fourth output t/r switches 320-326 may be removed. In this example, the first through fourth cross-point switches 360-366 would be used as bi-directional switches, connecting the selected group of transducer elements 104 to the system transmitters 102 and receivers 108, during both of the transmit and receive operations. This embodiment thus requires less electronics.

Figure 12:
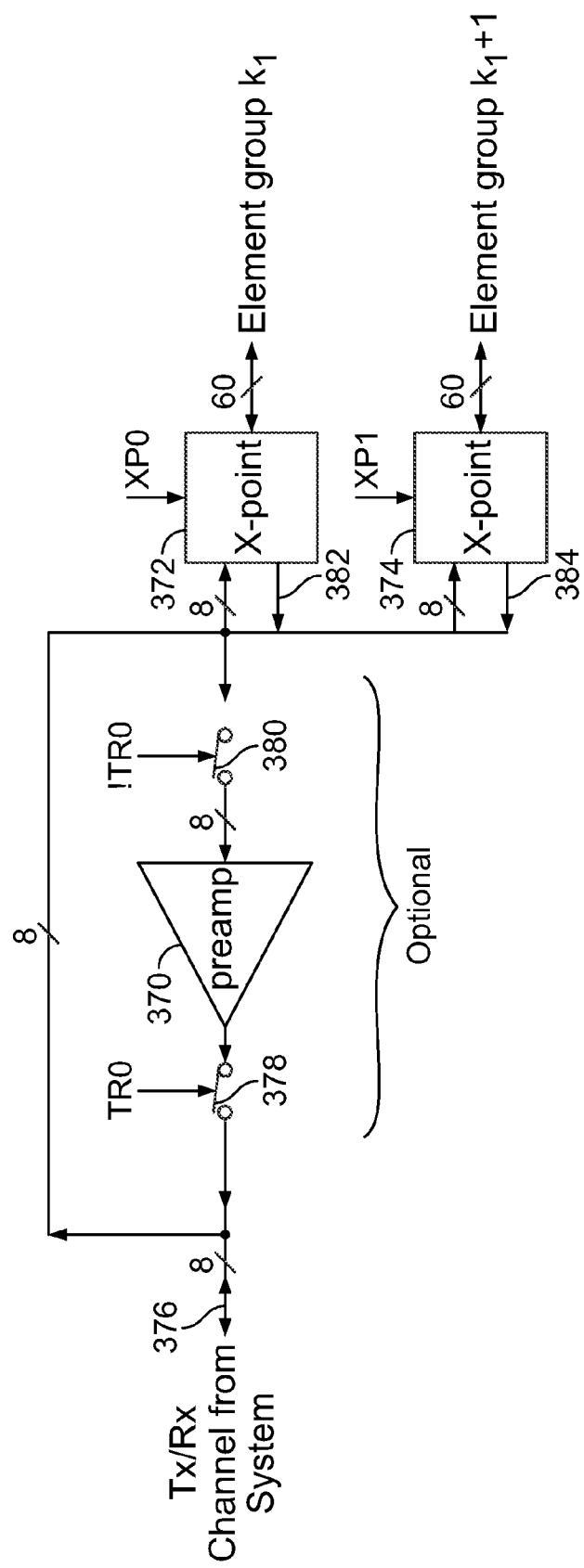
FIG. 12 is a schematic block diagram of cross-point switches being used for both transmit and receive operations in accordance with an embodiment of the present invention.

FIG. 12 illustrates an example of using cross-point switches to connect the system channels to the transmit and receive sub-apertures for the transmit and receive operations, respectively. Optionally, a preamplifier 370 may be placed between cross-point switches 372 and 374 and channel group 376. Transmit/receive switches 378 and 380 may be placed on either side of the optional preamplifier 370 and may be opened during the transmit operation and closed during the receive operation. When receiving signals, the cross-point switch 372 may be programmed to connect the transducer elements 104 within receive sub-apertures comprising the element group $k_1$ to one of the first through fourth channels such as first channel 382, and the cross-point switch 374 may be programmed to connect the transducer elements 104 within receive sub-apertures comprising the element group $k_1+1$ to, for example, second channel 384. The cross-point switches 372 and 374 may use a set receive configuration for assigning the transducer elements 104 to a specific channel during the receive operation that is different than the transmit configuration.

Figure 13:
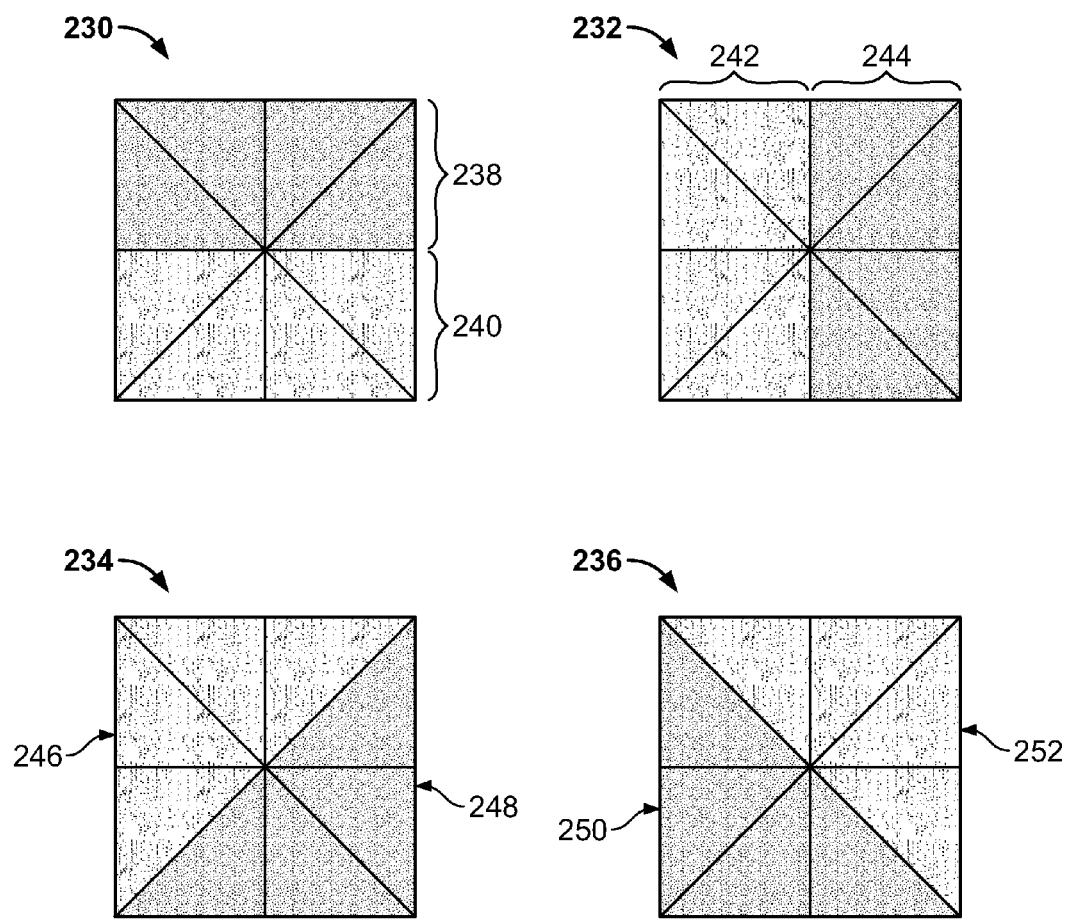
FIG. 13 is a diagram illustrating four different sub-aperture configurations of the transmit sub-apertures that may be used to steer the ultrasound beams during transmission in accordance with an embodiment of the present invention.

FIG. 13 illustrates embodiments of four different configurations of the transmit sub-apertures that may be used to steer ultrasound beams during transmission. First, second, third and fourth transmit configurations 230, 232, 234 and 236 are shown. A transmit configuration may be selected based on at least the local steering direction for each transmit sub-aperture to steer the beams in the desired direction. In one embodiment, each group of four triangular receive sub-apertures may be connected to four system channels.

Referring again to FIG. 4, the transmit sub-aperture 180 is divided into the first and second element groups 198 and 200 that are arranged in a horizontal and stacked configuration with respect to each other. The configuration of FIG. 4 is illustrated as the first transmit configuration 230 wherein first element group 238 and second element group 240 are horizontal and stacked with respect to each other. The second transmit configuration 232 divides the transmit sub-apertures into first and second element groups 242 and 244 that are side-by-side with respect to each other. The third transmit configuration 234 divides the transmit sub-apertures diagonally into first and second element groups 246 and 248, and the fourth transmit configuration 236 divides the transmit sub-apertures diagonally into first and second element groups 250 and 252. By way of example only, the first transmit configuration 230 may steer the beam upward and downward with respect to the plane of the figure, the second transmit configuration 232 may steer the beam left and right, the third transmit configuration 234 may steer the beam towards upper left and lower right corners and the fourth transmit configuration 236 may steer the beam towards the upper right and lower left corners.

Figure 14:
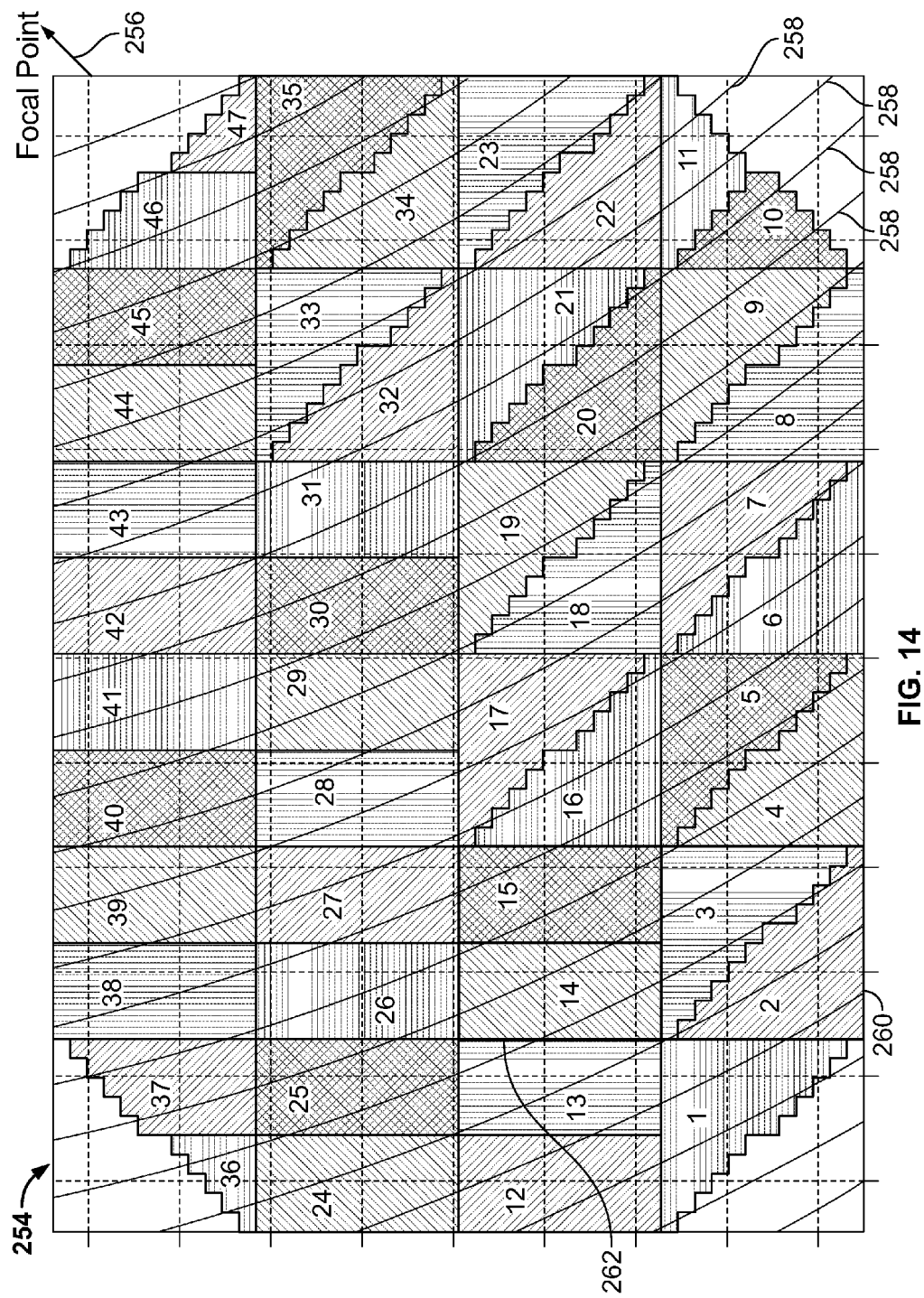
FIG. 14 is a diagram illustrating a transmit aperture with a projection of a focal point and associated delay lines indicating transducer element delays in accordance with an embodiment of the present invention.

FIG. 14 illustrates a transmit aperture 254 with a focal point 256 located outward away from the plane of the illustrated transmit aperture 254 and towards an upper right corner of the transmit aperture 254. In other words, the illustrated focal point 256 is the projection of the actual focal point location. The transmit aperture 254 is divided into a plurality of transmit sub-apertures, each having first and second transducer element groups. A plurality of delay lines 258 indicate areas through the transmit aperture 254 that have the same delay and the direction of the delay lines depends on the selected steering direction and focal point for the transmit beam. In this example, each of the transmit sub-apertures is individually configured to accomplish the desired steering with respect to the focal point 256. For example, the first sub-aperture 260 is configured in the fourth transmit configuration 236 and the second sub-aperture 262 is configured in the second transmit configuration 232.

Figure 15:
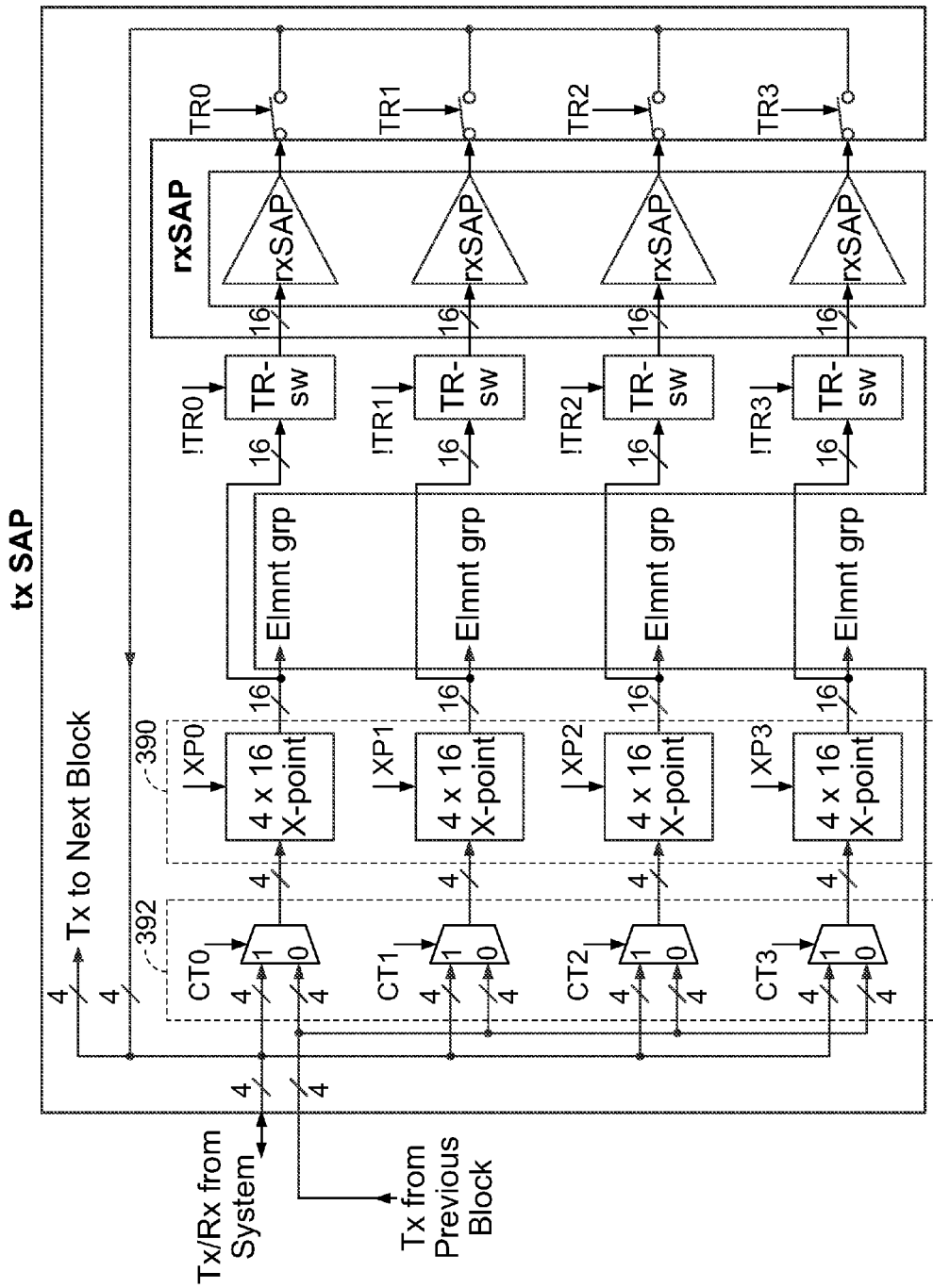
FIG. 15 is a schematic block diagram of a hardware implementation for the transmit sub-aperture configurations of FIGS. 13 and 14 formed in accordance with an embodiment of the present invention.

FIG. 15 illustrates a hardware implementation for the embodiment of FIGS. 13 and 14. A smaller cross-point switch matrix 390 may be used and is preceded by a multiplexer matrix 392 that is programmed according to the desired group configuration (first transmit configuration 230, second transmit configuration 232, etc.). The transmit current that flows through the multiplexer matrix 392 is much higher than the current that flows through the cross-point switch matrix 390. Therefore, the on-resistance of the multiplexer matrix 392 may be less than the on-resistance of the cross-point switches within the cross-point switch matrix 390 by, for example, at least a factor of 4. The transducer element 104 to channel delay assignments and switch programming may be determined as previously described in connection with FIG. 8.

Figure 16:
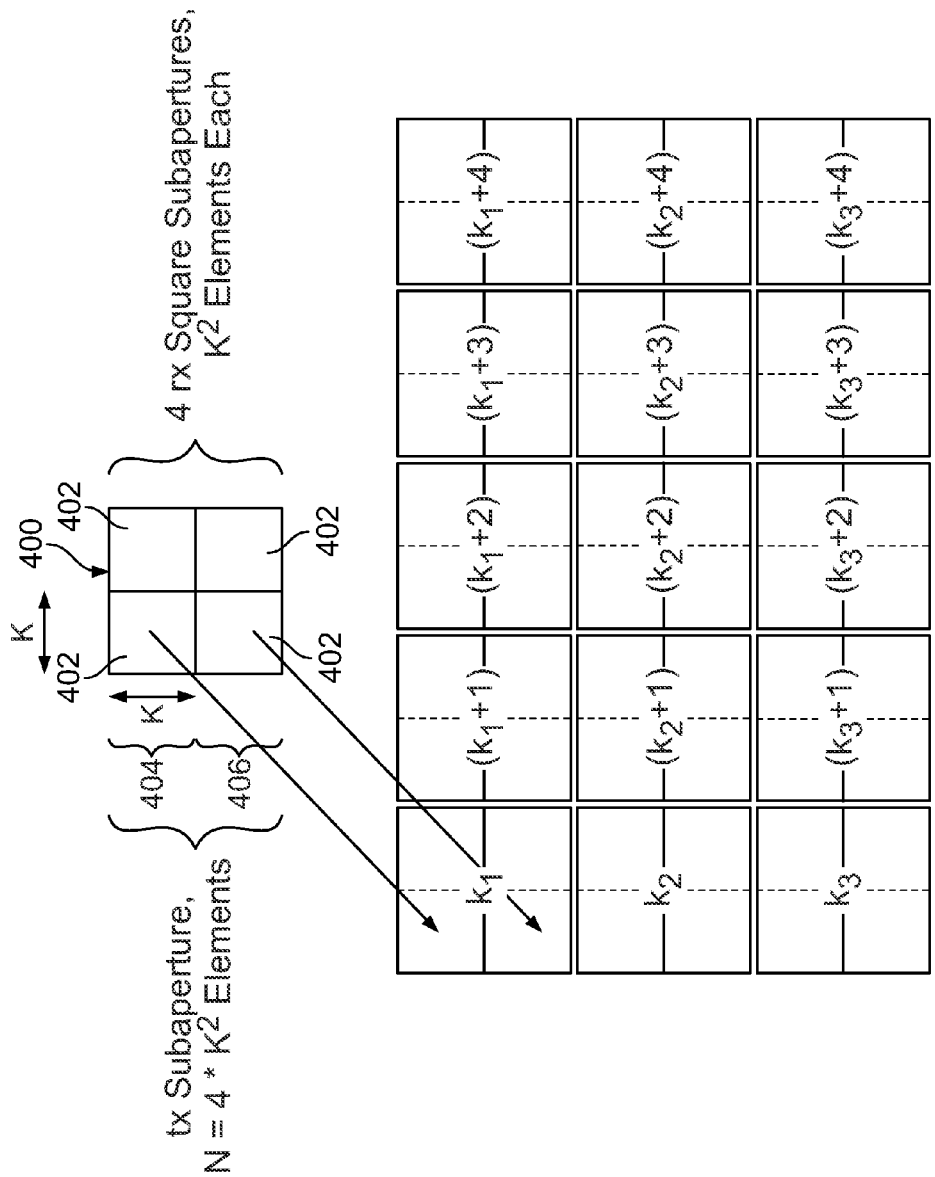
FIG. 16 is a diagram illustrating a transmit sub-aperture having a plurality of square receive sub-apertures in accordance with an embodiment of the present invention.

FIG. 16 illustrates an embodiment wherein a transmit sub-aperture 400 comprises a plurality of square receive sub-apertures 402. In this example, each transmit sub-aperture 400 has four receive sub-apertures 402. The transmit sub-aperture 400 may be divided into first and second element groups 404 and 406 as previously discussed in FIG. 4. The first and second element groups 404 and 406 are illustrated in the first transmit configuration 230 (as shown in FIG. 13) and may also be configured in the second transmit configuration 232.

A technical effect of at least one embodiment is partitioning the transducer elements of a probe into non-overlapping rectangular transmit sub-apertures during the transmit operation to steer the transmit beam in a desired direction. Each of the transmit sub-apertures may include more than one receive sub-aperture. The transmit sub-apertures may be individually configured into different transmit configurations. To reduce delay errors, the transducer elements within each transmit sub-aperture are mapped to a system channel based on the delay of the particular transducer element.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. An ultrasound system comprising:
   a probe including a two-dimensional (2D) array of transducer elements that form an aperture having a plurality of elements that are configured to transmit ultrasound signals, the transducer elements forming at least one transmit sub-aperture that is configured to be interconnected with a fixed group of the transducer elements within the aperture;

transmitters for generating electrical transmit signals; and
at least one transmit sub-aperture processor (tx SAP) configured to map different element groups of the transducer elements within the fixed group of the transducer elements to the transmitters to provide different transmit configurations based on a beam steering direction.

2. The ultrasound system of claim 1, wherein
the at least one tx SAP comprises a cross-point switch, and wherein the different element groups include first and second element groups and the different transmit configurations include first and second transmit configurations, and the system further comprising:
system channels interconnected with the transmitters through the cross-point switch for conveying the transmit signals there-between; and
a SAP controller configured to control the cross-point switch to select the first and second element groups of the transducer elements within the fixed group of the transducer elements to be driven by one of the system channels based on the first and second transmit configurations, respectively.

3. The ultrasound system of claim 1, further comprising:
system channels interconnected with the transmitters for conveying the transmit signals; and
a processor configured to determine delays associated with each of the transducer elements within the fixed group of the transducer elements, the delays being based at least on the beam steering direction, the at least one tx SAP being configured to assign at least one of the transducer elements within the fixed group of transducer elements to one channel of the system channels based on the delays.

4. The ultrasound system of claim 1, further comprising a plurality of receive elements configured to form receive sub-apertures, a cross-point switch, system channels interconnected with the transmitters and the cross-point switch for conveying the transmit signals there-between, and at least one receive sub-aperture processor (rx SAP) configured to control the cross-point switch to connect at least some of the system channels to the receive sub-apertures for receive operations.

5. The ultrasound system of claim 4, the system further comprising a SAP controller configured to divide the receive elements of the at least one transmit sub-aperture into two element groups that are oriented with respect to each other by one of horizontally, vertically or diagonally, the two element groups forming different transmit configurations for steering the transmit signals in different directions.

6. The ultrasound system of claim 1, wherein the at least one tx SAP comprises at least one cross-point switch for interconnecting the different element groups of the fixed group of the transducer elements and the transmitters, the at least one cross-point switch having at least one switch for each of the transducer elements within the fixed group of the transducer elements.

7. The ultrasound system of claim 1, further comprising:
system channels for conveying the transmit signals between the transmitters and the at least one tx SAP; and
a processor being configured to determine a maximum delay and a minimum delay based at least on the beam steering direction and delays associated with the transducer elements within the fixed group of transducer elements, the processor further configured to determine intermediate delays based on at least the maximum and minimum delays, the processor assigning one of the maximum delay, the minimum delay and the intermediate delays to each of the system channels.

8. The ultrasound system of claim 1, further comprising:
receivers for receiving electrical receive signals;
system channels for conveying the transmit signals between the transmitters and the at least one tx SAP;
the tx SAP comprising at least one cross-point switch for interconnecting a group of the system channels with the fixed group of transducer elements; and
preamplifiers for receiving the receive signals from the cross-point switch, the system channels further configured to convey the receive signals between the preamplifiers and the receivers.

9. The ultrasound system of claim 1, wherein the different element groups include first and second element groups and the different transmit configurations include first and second transmit configurations, wherein the at least one tx SAP maps the first element group of the fixed group of the transducer elements to the transmitters when in the first transmit configuration and maps the second element group of the fixed group of the transducer elements to the transmitters when in the second transmit configuration.

10. The ultrasound system of claim 1, further comprising system channels interconnected with the transmitters, wherein the at least one tx SAP comprises a cross-point switch to connect each of the transducer elements in the fixed group to any of the associated system channels.

11. An ultrasound system comprising:
a probe including a 2D array of transducer elements that form an aperture having a plurality of elements that are configured to transmit ultrasound signals;
at least one configurable cross-point switch having first and second sides, the at least one configurable cross-point switch being interconnected with a fixed group of the transducer elements on a first side, the fixed group of the transducer elements forming a transmit sub-aperture configured to transmit ultrasound signals;
system channels configured to convey at least the transmit ultrasound signals, the system channels interconnecting with the at least one configurable cross-point switch on the second side, the at least one configurable cross-point switch comprising at least one switch associated with each of the transducer elements within the fixed group of the transducer elements, the at least one configurable cross-point switch connecting at least one of the transducer elements with one of the system channels; and
a sub-aperture processor (SAP) controller configured to control the at least one configurable cross-point switch to map different element groups of the transducer elements within the fixed group of transducer elements to the system channels to provide different transmit configurations based on delays associated with ultrasound transmit signals.

12. The ultrasound system of claim 11, wherein the transmit sub-aperture is divided into at least first and second receive sub-apertures, wherein the first and second receive sub-apertures comprise first and second predetermined subsets of transducer elements from within the fixed group of transducer elements for receiving the ultrasound signals.

13. The ultrasound system of claim 11, wherein the transmit sub-aperture is divided into at least first and second receive sub-apertures, wherein the first and second receive sub-apertures comprise first and second predetermined subsets of transducer elements from within the fixed group of transducer elements, wherein the at least one configurable cross-point switch is further configured to map the first and second predetermined subsets of transducer elements to a first system channel and a second system channel, respectively, from within the system channels for receiving the ultrasound signals.

14. The ultrasound system of claim 11, wherein the SAP controller is further configured to determine a maximum delay and a minimum delay based at least on a delay associated with each of the transducer elements, the SAP controller further configured to determine intermediate delays based on at least the maximum and minimum delays, the SAP controller further con figured to assign one of the maximum delay, the minimum delay and the intermediate delays to each of the system channels.

15. The ultrasound system of claim A, further comprising:
   at least one receive SAP for processing the received ultrasound signals detected by the plurality of receive elements;
   a receive SAP die including the at least one receive SAP; and
   a transmit SAP die including the at least one configurable cross-point switch and further comprising input and output switches, the input switches inputting the receive ultrasound signals to the at least one receive SAP and the output switches receiving output signals from the at least one receive SAP.

16. The ultrasound system of claim 11, wherein the at least one configurable cross-point switch comprises at least one switch for each of the transducer elements within the group.

17. The ultrasound system of claim 11, wherein the different element groups include first and second element groups and the different transmit configurations include first and second transmit configurations, wherein the SAP controller controls the at least one cross-point switch to map the first element group of the fixed group of the transducer elements to the transmitters when in the first transmit configuration and to map the second element group of the fixed group of the transducer elements to the transmitters when in the second transmit configuration.

18. The ultrasound system of claim 11, wherein the SAP controller controls the at least one configurable cross-point switch to connect each of the transducer elements in the fixed group to any of the associated system channels.

* * * * *